(12) United States Patent  (10) Patent No.: US 6,339,229 B1
Shiga et al.  (45) Date of Patent: Jan. 15, 2002

(54) TEST STRUCTURE FOR INSULATION-FILM EVALUATION

(75) Inventors: Katsuya Shiga; Naofumi Murata, both of Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/531,523

(22) Filed: Mar. 21, 2000

(30) Foreign Application Priority Data

Oct. 21, 1999 (JP) .......................................... P11-299295

(51) Int. Cl.[7] .......................... H01L 21/66; H01L 23/58
(52) U.S. Cl. ........................ 257/48; 257/215; 257/235; 257/239
(58) Field of Search ........................... 257/48, 214–216, 257/235–239

(56) References Cited

U.S. PATENT DOCUMENTS 4,521,797 A * 6/1985 Oda ........................... 257/222
4,763,198 A * 8/1988 Tabei .......................... 348/322
5,416,419 A * 5/1995 Witt ............................ 324/551
5,841,164 A * 11/1998 Tsujino ........................ 257/316

FOREIGN PATENT DOCUMENTS

DE     211 413 A  *  7/1984  .......... G01R/31/02
JP     9-129695       5/1997

* cited by examiner

Primary Examiner—Allan R. Wilson
(74) Attorney, Agent, or Firm—Oblon, Spivak, McClelland, Maier & Neustadt, P.C.

(57) ABSTRACT

A test structure for insulation-film evaluation has a CCD structure comprising a semiconductor substrate (1), a gate insulating film (2) to be evaluated which is formed across the main surface of the semiconductor substrate (1), a plurality of gate electrodes (3*a*–3*i*) equally spaced in this order on the gate insulating film (2), a wire (20) connected to the gate electrodes (3*a*, 3*d*, 3*g*), a wire (21) connected to the gate electrodes (3*b*, 3*e*, 3*h*), and a wire (22) connected to the gate electrodes (3*c*, 3*f*, 3*i*). The test structure further comprises a read circuit (5) including an inverter (4) and other elements connected to the output stage of the CCD structure. This test structure allows simple failure location.

17 Claims, 14 Drawing Sheets

TEST STRUCTURE FOR INSULATION-FILM EVALUATION

BACKGROUND OF THE INVENTION

1. Field of the Invention

The present invention relates to a test structure for reliability evaluation of an insulation film such as a gate insulating film.

2. Description of the Background Art

Generally, a technique called "Time Depend Dielectric Breakdown (TDDB)" is used for reliability evaluation of an insulation film such as a gate insulating film. FIG. 28 is a cross-sectional view of a conventional test structure for insulation-film evaluation used in the TDDB test. A gate insulating film 102 to be evaluated is formed across the surface of a substrate 101 and a gate electrode 103 is formed across the surface of the gate insulating film 102. The TDDB test is conducted using an evaluation pattern such as a pattern including the edge of the active region (field edge), a pattern including the gate edge, and a flat pattern consisting only of surface components, thereby evaluating process damage to the gate insulating film with respect to each component. For instance, the TDDB test using a gate edge pattern evaluates how the gate insulating film receives damage from etching in forming a gate electrode.

The TDDB test for a certain period of time causes a dielectric breakdown in the gate insulating film at any rate. The reliability of the gate insulating film is evaluated by means of statistical processing of such a fault-time distribution. To clarify the physical cause of failures, however, failure analysis is absolutely necessary.

According to a failure analysis technique using the conventional test structure for insulation-film evaluation, failure analysis is performed in the following two steps: (1) finding the physical location of a failure using an emission analyzer or an electron beam tester, for example; and (2) observing the failure using a scanning electron microscopy (SEM), for example. This technique has a problem that especially the former step is complicated.

SUMMARY OF THE INVENTION

A first aspect of the present invention is directed to a test structure for insulation-film evaluation comprising: a substrate; an insulation film to be evaluated which is formed on a main surface of the substrate; an electrode array formed on the insulation film and consisting of a plurality of electrodes arranged in spaced manner, a plurality of wires for applying a voltage to the plurality of electrodes, the voltage including a voltage for applying evaluation stress to the insulation film and a voltage for sequentially transferring charge generated in breakdown part of the insulation film along the electrode array to detect the presence or absence of breakdown in the insulation film due to the application of the evaluation stress; and a read circuit for sequentially reading the presence or absence of the transfer of the charge.

According to a second aspect of the present invention, in the test structure of the first aspect, adjacent three of the electrodes in the electrode array are connected to different ones of the wires.

According to a third aspect of the present invention, in the test structure of the first aspect, the electrode array consists of the electrodes under which an impurity region is formed in the main surface of the substrate and the electrodes under which the impurity region is not formed in the main surface of the substrate, which are aligned alternately.

According to a fourth aspect of the present invention, in the test structure of the first aspect, the electrode array consists of the electrodes doped with impurities and the electrodes not doped with the impurities, which are aligned alternately.

According to a fifth aspect of the present invention, in the test structure of the first aspect, adjacent four of the electrodes in the electrode array are connected to different ones of the wires.

According to a sixth aspect of the present invention, in the test structure of the first aspect, the electrode array consists of first electrodes and second electrodes which are aligned alternately, the first electrodes formed on a thin-film portion of the insulation film having a first thickness, the second electrodes formed on a thick-film portion of the insulation film having a second thickness larger than the first thickness; and adjacent four of the electrodes in the electrode array are connected to different ones of the wires.

According to a seventh aspect of the present invention, in the test structure of the sixth aspect, the second electrodes extend over the end portions of the first electrodes.

According to an eighth aspect of the present invention, in the test structure of the first aspect, a plurality of impurity regions with different impurity concentrations are adjacently formed in the main surface of the substrate under each of the electrodes.

According to a ninth aspect of the present invention, the test structure of either of the first to eighth aspects further comprises: a drawn region formed along the electrode array in the main surface of the substrate, for drawing charge flowing out of a potential well under breakdown part of the insulation film caused by the application of the evaluation stress.

According to a tenth aspect of the present invention, in the test structure of either of the first to ninth aspects, the substrate includes an element isolation region where an element isolation insulation film is formed, and an active region defined by the element isolation insulation film; and the end portions of the electrodes are within the active region.

According to an eleventh aspect of the present invention, in the test structure of either of the first to ninth aspects, the substrate includes an element isolation region where an element isolation insulation film is formed, and an active region defined by the element isolation insulation film; and the electrodes extend over a boundary between the element isolation region and the active region.

According to a twelfth aspect of the present invention, in the test structure of either of the first to eleventh aspects, cells including the electrodes are arranged in the form of a matrix, all of the cells being electrically connected to each other by an active region of the substrate.

According to a thirteenth aspect of the present invention, in the test structure of either of the first to eleventh aspects, cells including the electrodes are arranged in the form of a matrix, a plurality of the cells being divided into a plurality of groups by an element isolation region of the substrate; and the read circuit is provided for each of the groups.

A fourteenth aspect of the present invention is directed to a test structure for insulation-film evaluation, comprising: a substrate; an insulation film to be evaluated which is formed on a main surface of the substrate; an electrode matrix consisting of a plurality of electrodes formed in the form of a matrix on the insulation film; a stress applying circuit for applying evaluation stress to the insulation film; a first shift register capable of applying a voltage to the plurality of electrodes for each column of the electrode matrix; and a second shift register which is electrically connected to the substrate for each row of the electrode matrix and capable of detecting whether or not the application of the voltage by the first register causes current flow to the substrate through the insulation film.

According to a fifteenth aspect of the present invention, in the test structure of the fourteenth aspect, the electrode matrix includes at least two rows having the insulation film of different thicknesses.

According to a sixteenth aspect of the present invention, in the test structure of either of the first to fifteenth aspects, cells including the electrodes are arranged in the form of a matrix; and a mark is provided at predetermined blocks on the substrate.

The test structure for insulation-film evaluation of the first aspect adopts the CCD structure, wherein the charge supplied into the substrate due to a breakdown of the insulation film is sequentially transferred so that the read circuit can locate a failure. This structure simplifies failure location in the insulation film as compared to a conventional technique of locating failures using an emission analyzer, for example.

In the test structure of the second aspect, three-phase charge transfer allows failure location in the insulation film.

In the test structure of the third aspect, the impurity regions formed in the main surface of the substrate provides the potential difference between adjacent cells. This enables two-phase charge transfer.

In the test structure of the fourth aspect, the impurities introduced into the electrodes provides the potential difference between adjacent cells. This enables two-phase charge transfer.

In the test structure of the fifth aspect, the voltage of different magnitudes, which is applied from the outside to the electrodes through the wires, provides the potential difference between adjacent cells. This enables two-phase charge transfer.

In the test structure of the sixth aspect, the insulation film of different thicknesses provides the potential difference between adjacent cells. This enables two-phase charge transfer.

The test structure of the seventh aspect eliminates a potential barrier to be an impediment to charge transfer.

In the test structure of the eighth aspect, the plurality of impurity regions with different impurity concentrations provides the potential difference. Accordingly, the charge supplied from breakdown part of the insulation film into the substrate can sequentially be transferred by simple two-phase operations using a two-input system. This allows the read circuit to find the locations of failures.

In the test structure of the ninth aspect, even if too much charge is supplied from breakdown part of the insulation film into the substrate and flows out of the potential well under the breakdown part, the overflowing charge can be drawn to the drawn region. This improves accuracy in failure location in the insulation film.

The test structure of the tenth aspect enables the TDDB test using a pattern including the gate edge.

The test structure of the eleventh aspect enables the TDDB test using a pattern including the field edge.

The test structure of the twelfth aspect requires only one read circuit. This results in simplification of the structure.

In the test structure of the thirteenth aspect, failure location can independently performed for each group. This improves accuracy in failure location.

In the test structure of the fourteenth aspect, a plurality of electrodes are arranged in the form of a matrix. The row and column of the electrode matrix in which the insulation film suffers a breakdown can be detected by varying combinations of selections by the first shift register and the second shift register. This simplifies specification of the locations of failures in the insulation film.

The fifteenth aspect allows a plurality of insulation films of different thicknesses to be evaluated using a single test structure.

In the test structure of the sixteenth aspect, for failure observations using an SEM, an operator can look to a mark on the test structure to recognize the locations of failures in the insulation film. This simplifies the operation of entering the detected failures within the visual field of the SEM.

An object of the present invention is to provide a test structure for insulation-film evaluation, which allows simple failure location.

These and other objects, features, aspects and advantages of the present invention will become more apparent from the following detailed description of the present invention when taken in conjunction with the accompanying drawings.

DESCRIPTION OF THE PREFERRED EMBODIMENTS

First Preferred Embodiment

Figure 1:
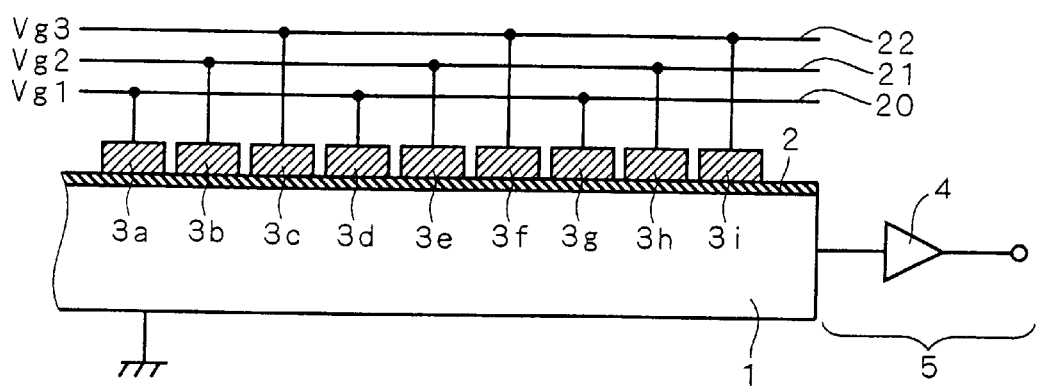
FIG. 1 is a cross-sectional view of a test structure for insulation-film evaluation according to a first preferred embodiment of the present invention.

FIG. 1 is a cross-sectional view of a test structure for insulation-film evaluation according to a first preferred embodiment of the present invention. As shown, the test structure of the first preferred embodiment has a CCD structure comprising a semiconductor substrate 1 connected to ground, a gate insulating film 2 to be evaluated which is formed across the main surface of the semiconductor substrate 1, a plurality of gate electrodes 3a to 3i equally spaced in this order on the gate insulating film 2, a wire 20 connected to the gate electrodes 3a, 3d, 3g, a wire 21 connected to the gate electrodes 3b, 3e, 3h, and a wire 22 connected to the gate electrodes 3c, 3f, 3i. Of a gate-electrode array consisting of the gate electrodes 3a to 3i, three adjacent gate electrodes are connected to different wires. The test structure of the first preferred embodiment further comprises a read circuit 5 which includes an inverter 4 and other elements connected to the output stage of the CCD structure. The read circuit 5 in FIG. 1 is located outside the semiconductor substrate 1, but in practice, it is formed in the semiconductor substrate 1.

Figure 2:
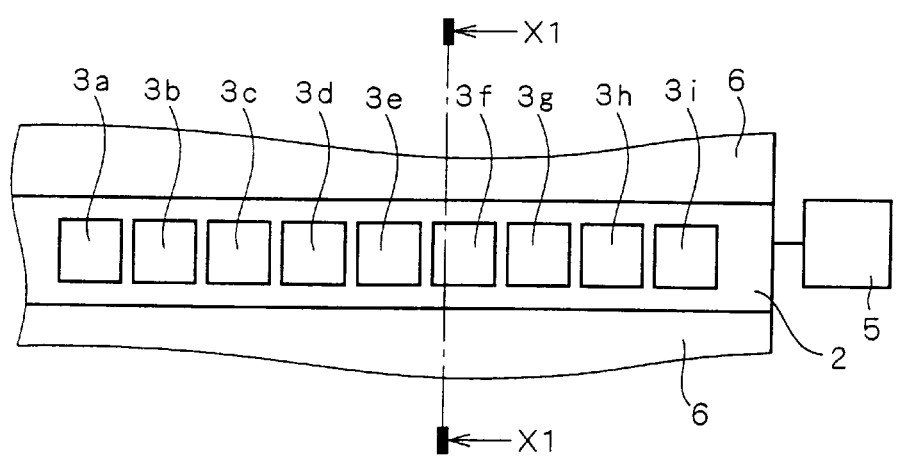
FIG. 2 is a top view of the test structure of the first preferred embodiment.
Figure 3:
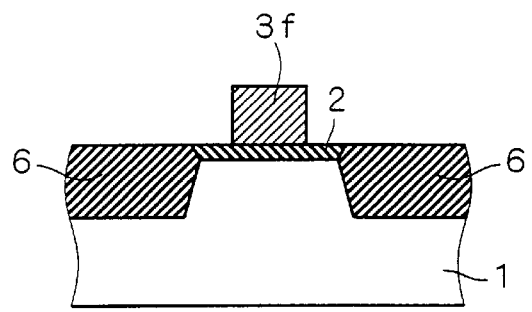
FIG. 3 is a cross-sectional view taken along the line X1 in FIG. 2.

FIG. 2 is a top view of the test structure of the first preferred embodiment, and FIG. 3 is a cross-sectional view taken along the line X1 in FIG. 2. The wires 20 to 22 in FIG. 1 are not shown. As shown in FIGS. 2, 3, the semiconductor substrate 1 is provided with an element isolation insulation film 6 to define an element forming region (hereinafter referred to as an "active region"). The gate insulating film 2 and the gate electrodes 3a to 3i are formed on the semiconductor substrate 1 in the active region.

Now, we will describe a technique of the TDDB test using the test structure of the first preferred embodiment. First, a voltage of the same level is applied from an external power source through the wires 20 to 22 to the gate electrodes 3a to 3i (i.e., Vg1 =Vg2=Vg3 in FIG. 1), thereby to apply predetermined evaluation stress to the gate insulating film 2.

Figure 4:
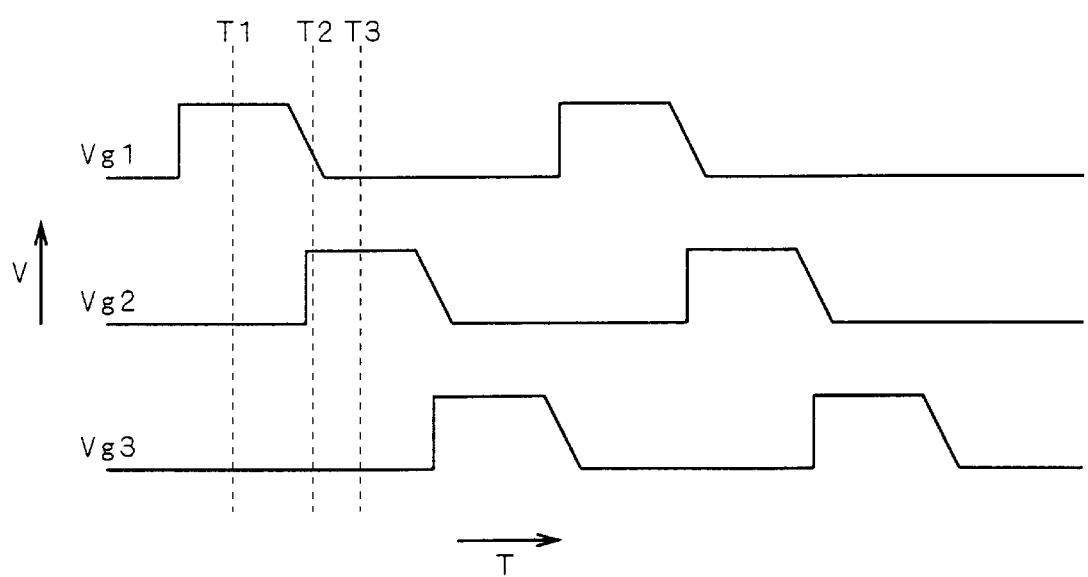
FIG. 4 is a timing chart showing the waveforms of voltages applied to the gate electrode.
Figure 5:
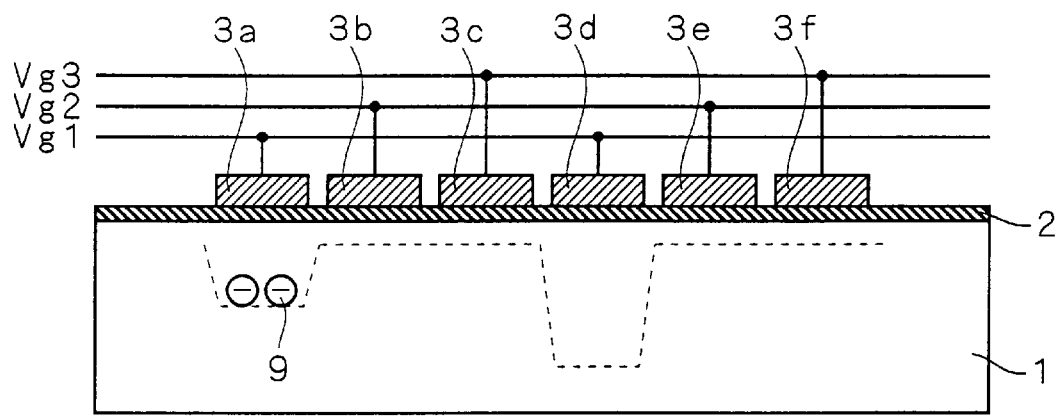
FIG. 5 is a cross-sectional view showing the inside of a semiconductor substrate at the time T1 in FIG. 4.
Figure 6:
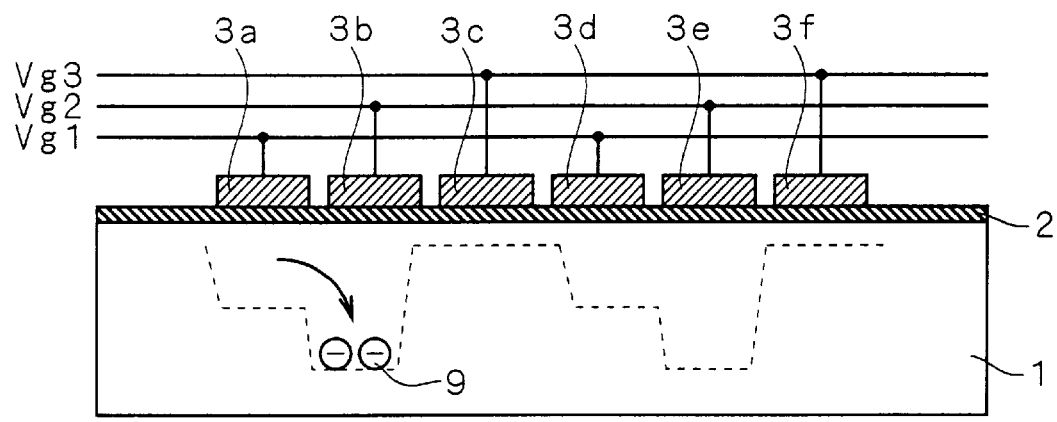
FIG. 6 is a cross-sectional view showing the inside of the semiconductor substrate at the time T2 in FIG. 4.
Figure 7:
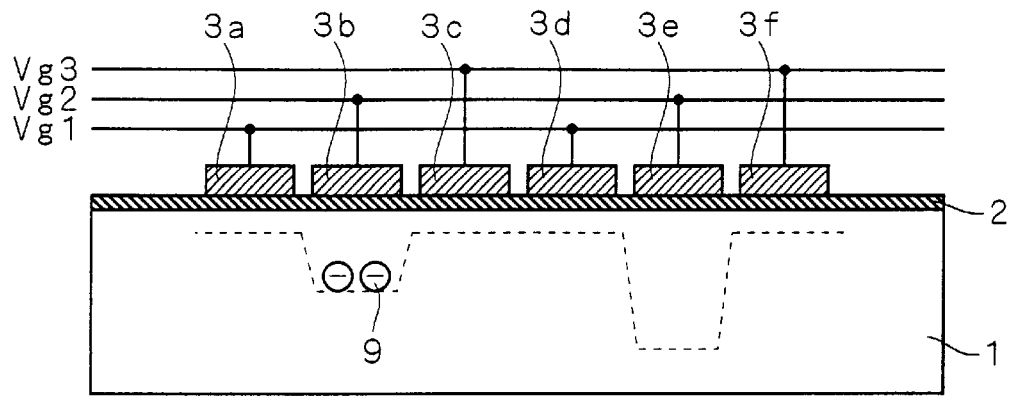
FIG. 7 is a cross-sectional view showing the inside of the semiconductor substrate at the time T3 in FIG. 4.

Next is to find the locations of failures. FIG. 4 is a timing chart showing the waveforms of voltages Vg1, Vg2, Vg3 applied to the gate electrodes 3a to 3i for failure location. FIGS. 5 to 7 are cross-sectional views showing the inside of the semiconductor substrate 1 at the times T1 to T3 in FIG. 4, respectively. We assume that the gate insulating film 2 under the gate electrode 3a is faulty.

At the time T1, in the failed part of the gate insulating film 2, charge 9 is supplied into the semiconductor substrate 1 by the application of the voltage Vg1 as shown in FIG. 5. In the other part of the gate insulating film 2, there is no supply of the charge 9 and only a depletion layer spreads in the depth direction of the semiconductor substrate 1. At the time T2, as shown in FIG. 6, the depletion layer under the gate electrodes 3b, 3e is spread by the application of the voltage Vg2 and the charge 9 transfers from under the gate electrode 3a to under the gate electrode 3b. At the time T3, the depletion layer under the gate electrode 3b shrinks by the influence of the charge 9 as shown in FIG. 7. Eventually, the charge 9 transfers from the condition of FIG. 5 to the right by one gate electrode. By repetition of these operations, the charge 9 supplied from the locations of failures in the gate insulating film 2 into the semiconductor substrate 1 can sequentially be transferred to the output stage in the interior of the semiconductor substrate 1.

The threshold voltage of the inverter 4, constituting the read circuit 5, is preset so as to go high/low depending on the presence or absence of the charge 9 transferred sequentially. The read circuit 5 is activated in line with the input pulse to count the number of pulses. Accordingly, which part of the gate insulating film 2 is faulty can be found.

In this fashion, the test structure of the first preferred embodiment adopts the CCD structure, wherein the charge 9 supplied into the semiconductor substrate 1 due to a failure in the gate insulating film 2 is transferred sequentially so that the read circuit 5 can locate the failure. This structure allows simple failure location in the gate insulating film 2 as compared to the conventional technique of locating failures using an emission analyzer, for example.

Figure 8:
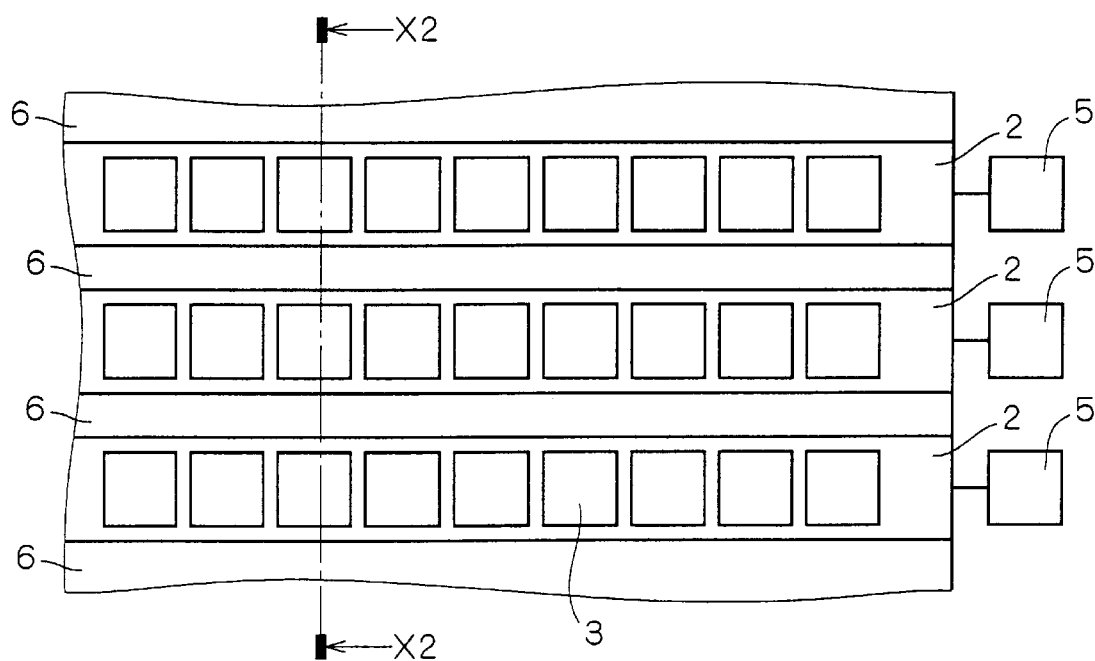
FIG. 8 is a top view showing a modification of the test structure of the first preferred embodiment.
Figure 9:
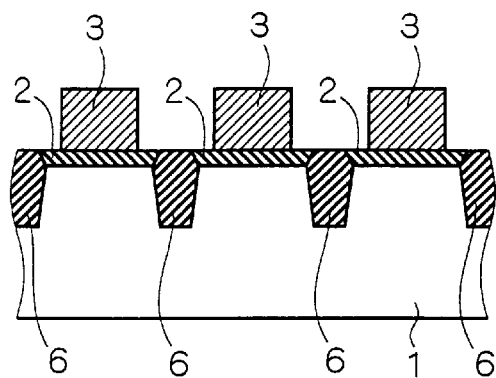
FIG. 9 is a cross-sectional view taken along the line X2 in FIG. 8.

FIG. 8 is a top view showing a modification of the test structure of the first preferred embodiment, and FIG. 9 is a cross-sectional view taken along the line X2 in FIG. 8. The wires 20 to 22 in FIG. 1 are not shown. When there are a plurality of gate-electrode arrays as shown in FIG. 8, the element isolation insulation film 6 provides electrical isolation between each row and one read circuit 5 is provided for each row. This structure allows failure location in the gate insulating film 2 for each row.

Second Preferred Embodiment

The aforementioned test structure of the first preferred embodiment is a three-phase CCD structure, but it may be a two-phase CCD structure.

Figure 10:
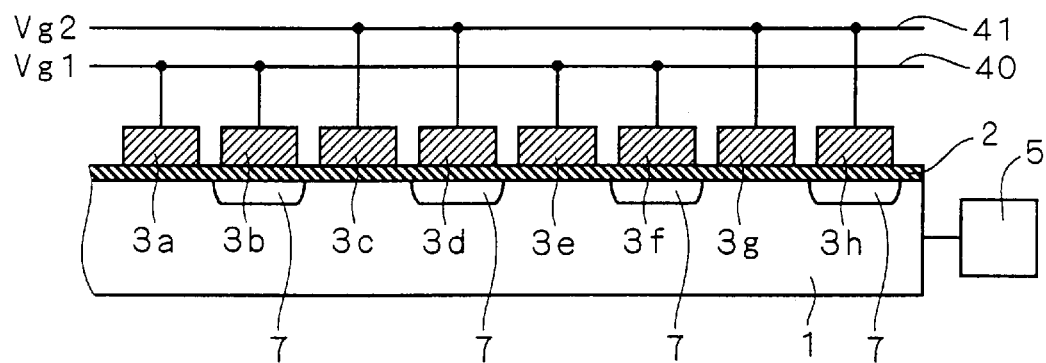
FIG. 10 is a cross-sectional view of a test structure for insulation-film evaluation according to a second preferred embodiment of the present invention.

FIG. 10 is a cross-sectional view of a test structure for insulation-film evaluation according to a second preferred embodiment of the present invention. Of a gate-electrode array consisting of a plurality of gate electrodes aligned on the gate insulating film 2, eight gate electrodes 3a to 3h aligned in this order are shown in FIG. 10. In the main surface of the semiconductor substrate 1 under the gate electrodes 3b, 3d, 3f, 3h, ion-implanted regions 7 are formed, which are doped with n-type impurities such as P and As or p-type impurities such as B. That is, the gate electrodes 3b, 3d, 3f, 3h with the ion-implanted regions 7 formed thereunder and the gate electrodes 3a, 3c, 3e, 3g with no ion-implanted regions 7 are arrayed alternately. This structurally provides the potential difference between adjacent cells. The gate electrodes 3a, 3b, 3e, 3f are connected to a wire 40, and the gate electrodes 3c, 3d, 3g, 3h are connected to a wire 41.

Figure 11:
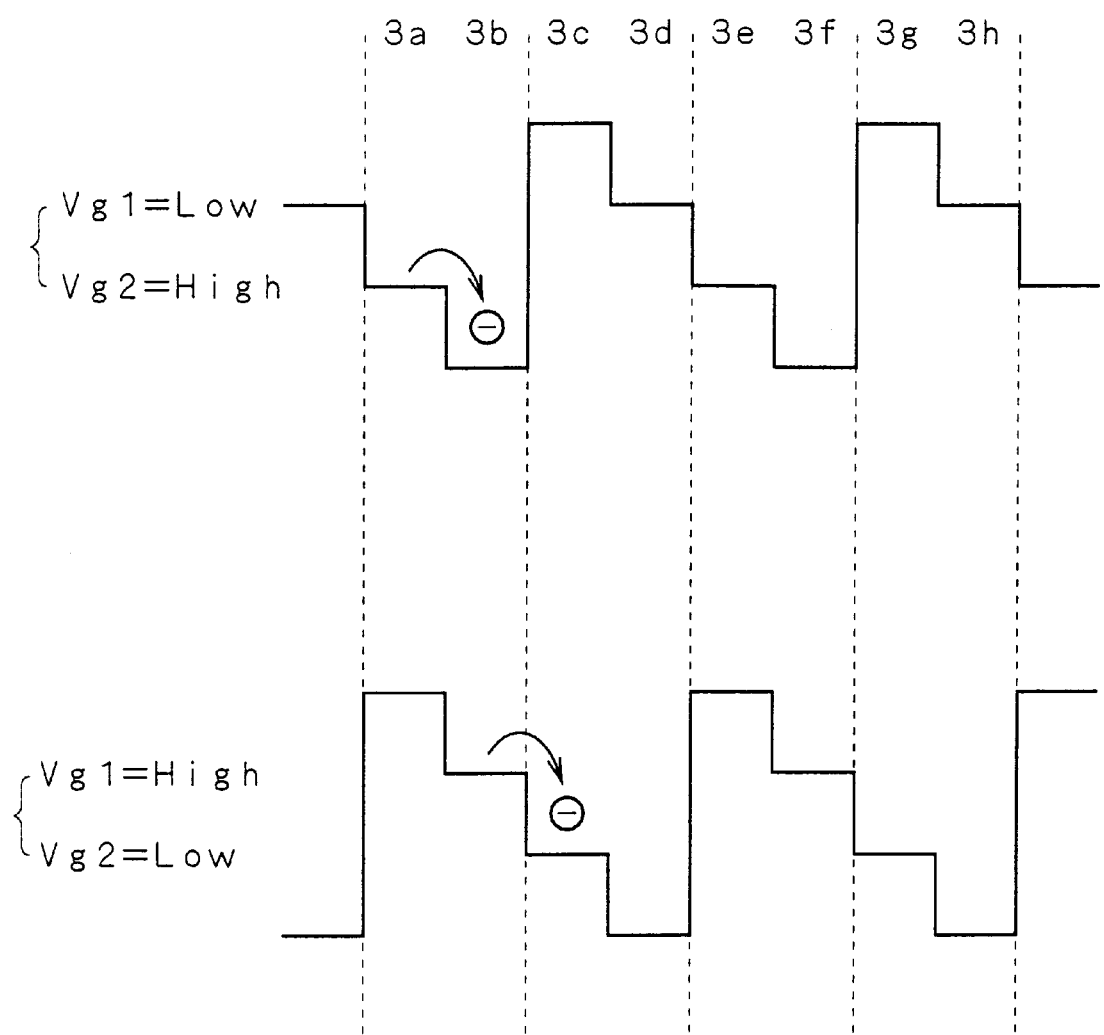
FIG. 11 is a schematic diagram showing an image of potential in the semiconductor substrate.

FIG. 11 is a schematic diagram showing an image of potential in the semiconductor substrate 1 when the voltages Vg1, Vg2 are applied to the wires 40, 41 for failure location. As above described, there is structurally the potential difference between a pair of cells which includes a pair of adjacent gate electrodes connected to the same wire (e.g., cells including the gate electrodes 3a, 3b). Therefore, by applying the voltages Vg1, Vg2, which go alternately high and low, to the gate electrodes 3a to 3h through the wires 40, 41, charge supplied from the locations of failures in the gate insulating film 2 into the semiconductor substrate 1 can sequentially be transferred to the output stage in the interior of the semiconductor substrate 1.

In the test structure of the second preferred embodiment, the gate-electrode array consisting of a plurality of gate electrodes comprises the gate electrodes 3b, 3d, 3f, 3h with the ion-implanted regions 7 formed thereunder and the gate electrodes 3a, 3c, 3e, 3g with no ion-implanted regions 7, which are aligned alternately. This structurally provides the potential difference between adjacent cells, thereby allowing failure location in the gate insulating film 2 by the two-phase charge transfer.

Figure 12:
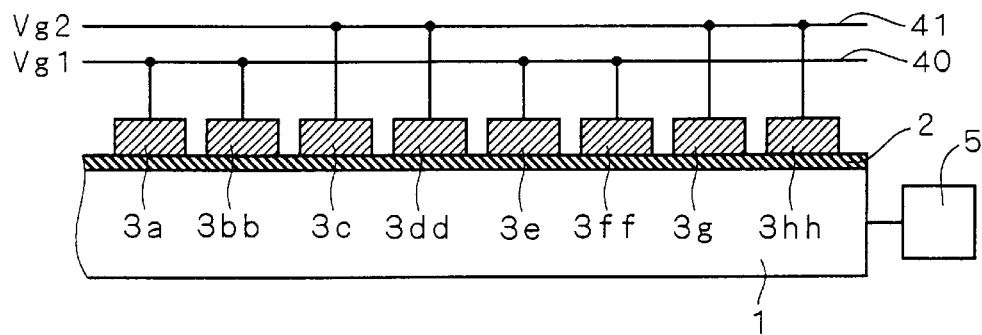
FIG. 12 is a cross-sectional view showing a first modification of the test structure of the second preferred embodiment.

FIG. 12 is a cross-sectional view showing a first modification of the test structure of the second preferred embodiment. Instead of forming the ion-implanted regions 7 shown in FIG. 10, the aforementioned n- or p-type impurities are introduced into the gate electrodes 3b, 3d, 3f, 3h, out of the gate electrodes 3a to 3h of polysilicon, to form gate electrodes 3bb, 3dd, 3ff, 3hh of doped polysilicon.

In this first modification of the test structure, the gate-electrode array consisting of a plurality of gate electrodes comprises the impurity-doped gate electrodes 3bb, 3dd, 3ff, 3hh and the undoped gate electrodes 3a, 3c, 3e, 3g, which are arrayed alternately. This structurally provides the potential difference between adjacent cells, thereby allowing failure location in the gate insulating film 2 by the two-phase charge transfer which is made by the application of the voltages Vg1, Vg2 as described above.

Figure 13:
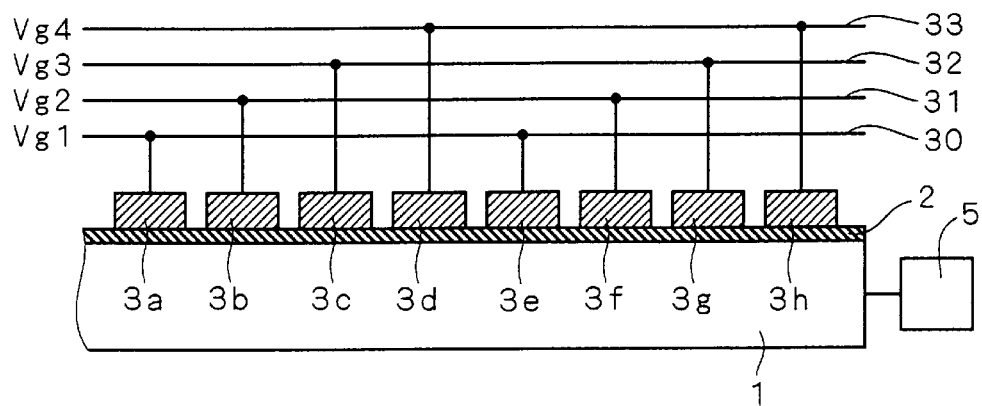
FIG. 13 is a cross-sectional view showing a second modification of the test structure of the second preferred embodiment.

FIG. 13 is a cross-sectional view showing a second modification of the test structure of the second preferred embodiment. To apply voltage to the gate electrodes 3a to 3h, four wires 30 to 33 are provided. The gate electrodes 3a, 3e are connected to the wire 30, the gate electrodes 3b, 3f to the wire 31, the gate electrodes 3c, 3g to the wire 32, and the gate electrodes 3d, 3h to the wire 33. Accordingly, adjacent four out of the gate electrodes 3a to 3h in the gate-electrode array are connected to different wires.

To apply evaluation stress to the gate insulating film 2, a common voltage is applied to the gate electrodes 3a to 3h (i.e., Vg1=Vg2=Vg3=Vg4). For failure location, the voltages Vg1, Vg2 are applied to the wires 30, 31 at a time under conditions of Vg1<Vg2, and the voltages Vg3, Vg4 are applied to the wires 32, 33 at a time under conditions of Vg3<Vg4. Accordingly, charge supplied from the locations of failures in the gate insulating film 2 into the semiconductor substrate 1 is sequentially transferred by two-phase operations. This allows the read circuit 5 to find the locations of failures.

In this second modification of the test structure, the voltage of different magnitudes, which is applied from the outside to the gate electrodes 3a to 3h, provides the potential difference between adjacent cells. The test structure is thus simple, allowing failure location in the gate insulating film 2 by the two-phase charge transfer.

Third Preferred Embodiment

Like the second preferred embodiment, a third preferred embodiment also adopts a two-phase CCD structure as the test structure for insulation-film evaluation.

Figure 14:
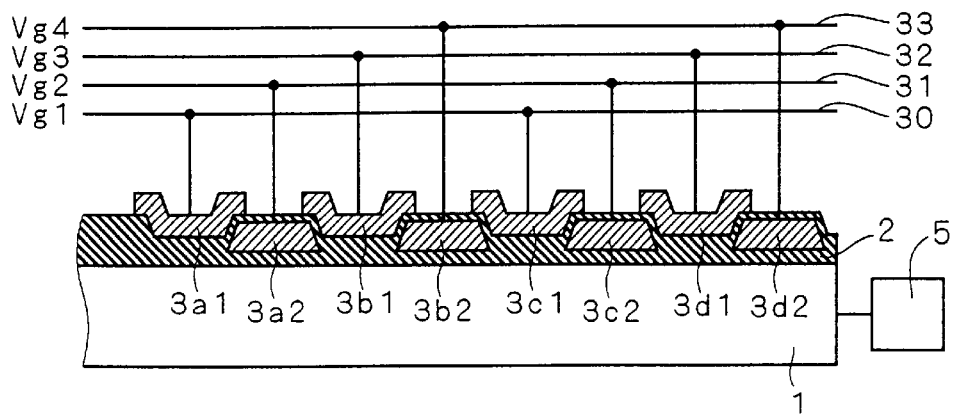
FIG. 14 is a cross-sectional view of a test structure for insulation-film evaluation according to a third preferred embodiment of the present invention.

FIG. 14 is a cross-sectional view of a test structure for insulation-film evaluation according to the third preferred embodiment. Of a gate-electrode array consisting of a plurality of gate electrodes aligned on the gate insulating film 2, four sets of gate electrodes 3a to 3d aligned in this order are shown in FIG. 14. The gate insulating film 2 includes a thin-film portion having a first thickness and a thick-film portion having a second thickness greater than the first thickness. Each of the gate electrodes 3a to 3d includes a first portion 3a2, 3b2, 3c2, 3d2 which is located on the thin-film portion of the gate insulating film 2 and a second portion 3a1, 3b1, 3c1, 3d1 which is located on the thick-film portion of the gate insulating film 2 and electrically isolated from the first portion 3a2, 3b2, 3c2, 3d2. The second portion 3a1, 3b1, 3c1, 3d1 extends to cover the end portions of the first portion 3a2, 3b2, 3c2, 3d2.

The wire 30 is connected to the second portion 3a1 of the gate electrode 3a and the second portion 3c1 of the gate electrode 3c. The wire 31 is connected to the first portion 3a2 of the gate electrode 3a and the first portion 3c2 of the gate electrodes 3c. The wire 32 is connected to the second portion 3b1 of the gate electrode 3b and the second portion 3d1 of the gate electrode 3d. The wire 33 is connected to the first portion 3b2 of the gate electrode 3b and the first portion 3d2 of the gate electrode 3d.

Now, we will describe a technique of the TDDB test using the test structure of the third preferred embodiment. First, voltages are applied from an external power source through the wires 30 to 33 to the gate electrodes 3a to 3d, thereby to apply predetermined evaluation stress to the gate insulating film 2. At this time, the voltage applied to the second portions 3a1, 3b1, 3c1, 3d1 on the thick-film portion of the gate insulating film 2 is higher than that applied to the first portions 3a2, 3b2, 3c2, 3d2 on the thin-film portion of the gate insulating film 2 (i.e., Vg1=Vg3>Vg2=Vg4).

Next is to find the locations of failures. The application of voltage under conditions of Vg1=Vg2, Vg3=Vg4 provides the potential difference between the first portions 3a2, 3b2, 3c2, 3d2 and the second portions 3a1, 3b1, 3c1, 3d1 due to the gate insulating film 2 of different thicknesses. Accordingly, the charge 9 supplied from the locations of failures in the gate insulating film 2 into the semiconductor substrate 1 is sequentially transferred by two-phase operations. This allows the read circuit 5 to find the locations of failures.

In the test structure of the third preferred embodiment, the second portions 3a1, 3b1, 3c1, 3d1 of the gate electrodes 3a to 3d cover the end portions of the respective first portions 3a2, 3b2, 3c2, 3d2. This eliminates a potential barrier to be an impediment to charge transfer.

Further, the four wires 30 to 33 are provided to apply voltages to the gate electrodes 3a to 3d. This four-input system for the input of voltage pulses to the gate electrodes 3a to 3d in readout enables the application of various patterns of voltage pulses from the outside.

Fourth Preferred Embodiment

In the test structures of the first to third preferred embodiments, the end portions of the gate electrodes 3a to 3i are within the active region as shown in FIG. 2. On the evaluation pattern basis, these structures correspond to TDDB evaluation using a gate edge pattern. A fourth preferred embodiment of the present invention, on the other hand, proposes a test structure for insulation-film evaluation used in TDDB evaluation using a field edge pattern including the edge of the active region.

Figure 15:
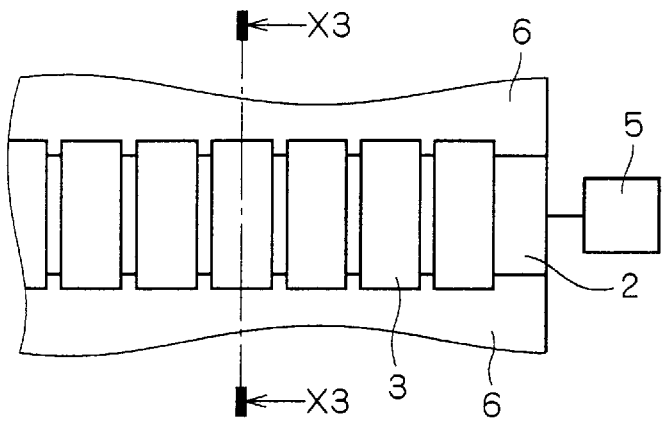
FIG. 15 is a top view of a test structure for insulation-film evaluation according to a fourth preferred embodiment of the present invention.
Figure 16:
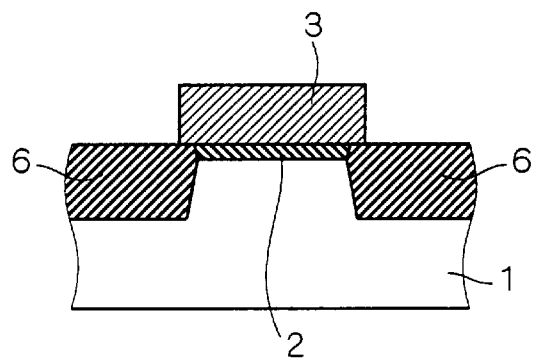
FIG. 16 is a cross-sectional view taken along the line X3 in FIG. 14.

FIG. 15 is a top view of the test structure of the fourth preferred embodiment, and FIG. 16 is a cross-sectional view taken along the line X3 in FIG. 15. Each of the gate electrodes 3 is formed on the gate insulating film 2, extending to the end portion of the element isolation insulation film 6. The edge of the active region is thus covered with the gate electrodes 3.

In the test structure of the fourth preferred embodiment, the width of the gate electrodes 3 is larger than that of the active region. This simplifies the test structure used in the TDDB evaluation using a field edge pattern.

Figure 17:
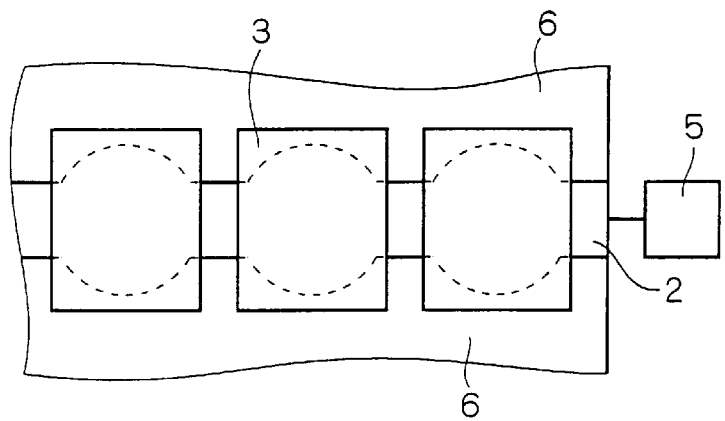
FIG. 17 is a top view showing a modification of the test structure of the fourth preferred embodiment.

FIG. 17 is a top view showing a modification of the test structure of the fourth preferred embodiment. In many of recent large-scale integrated devices consisting of cells (e.g., memory devices), the active region is peculiar in form for a higher level of integration (e.g., including circular components in contrast to a conventional one including only linear components). In the device of FIG. 17, the edge of the active region is partially circular. Each of the gate electrodes 3 extends over the element isolation insulation film 6, covering the edge of the active region including the circular portions. By arranging test structures which include various field edge components according to the form of the active region, batch evaluation with respect to those components becomes possible. This is ideally suitable as a test structure for reliability evaluation of recent mixed memory devices whose active regions have both the peculiar form for highly integrated memories and the conventional form for logic circuits.

Fifth Preferred Embodiment

Figure 18:
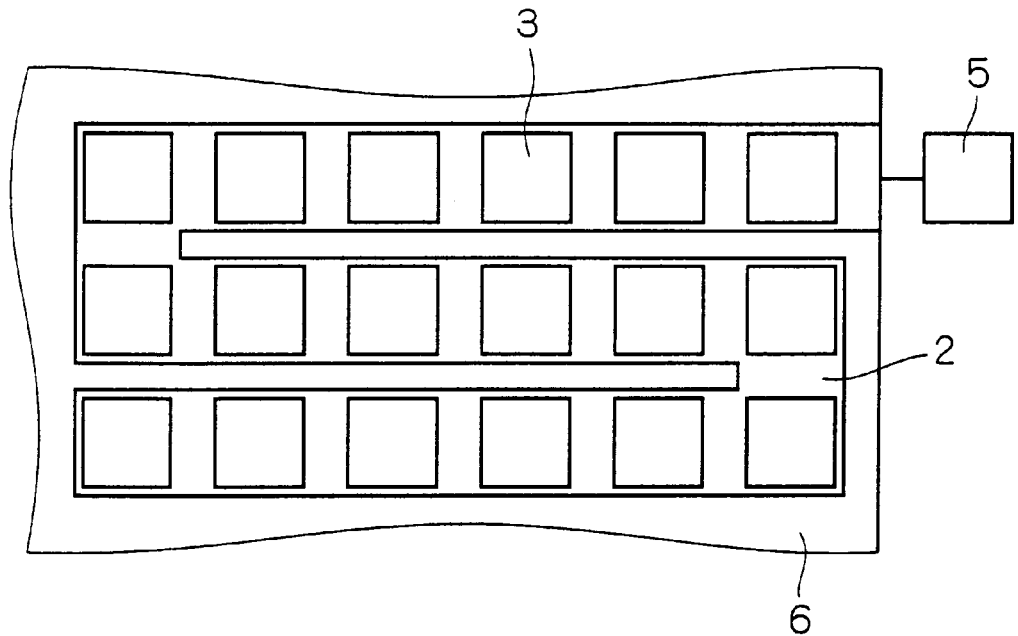
FIG. 18 is a top view of a test structure for insulation-film evaluation according to a fifth preferred embodiment of the present invention.

FIG. 18 is a top view of a test structure for insulation-film evaluation according to a fifth preferred embodiment of the present invention. A plurality of cells are arranged in the form of a matrix and the element isolation insulation film 6 is formed so that all the cells are connected in series by the active region. The presence or absence of the charge 9 transferred from each cell is sequentially detected by one read circuit 5 connected to the CCD structure.

Figure 19:
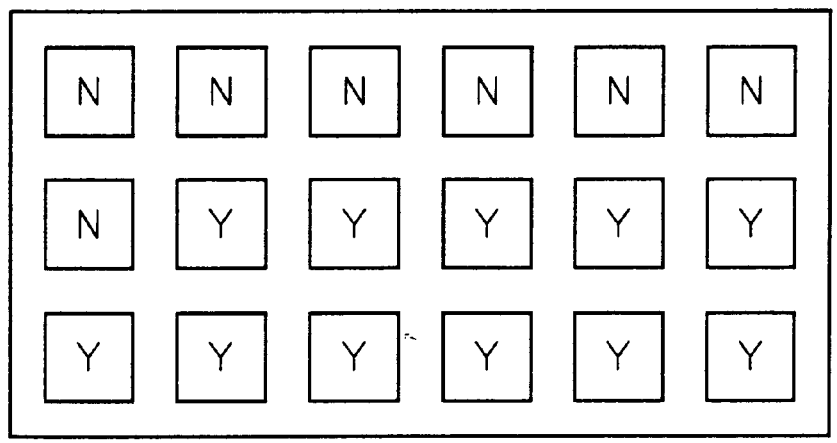
FIG. 19 shows a display matrix of the locations of failures.

FIG. 19 shows a display matrix of the locations of failures. As shown, a matrix similar to a physical matrix of cells is produced by a computer and displayed on the screen. Then, the detection result of charge transfer by the read circuit 5 (i.e., charge transfer (Y) or no charge transfer (N)) is displayed corresponding to each cell. This allows an operator to visually recognize the presence or absence of charge transfer, i.e., the locations of failures in the gate insulating film 2.

In the test structure of the fifth preferred embodiment, all the cells arranged in the form of a matrix are connected in series by the active region. Since the supply of charge 9 continues with the application of voltage at the locations of failures in the gate insulating film 2, the subsequent readout will always result in charge transfer (Y). This, however, simplifies the test structure since only a single read circuit 5 is required.

Sixth Preferred Embodiment

Figure 20:
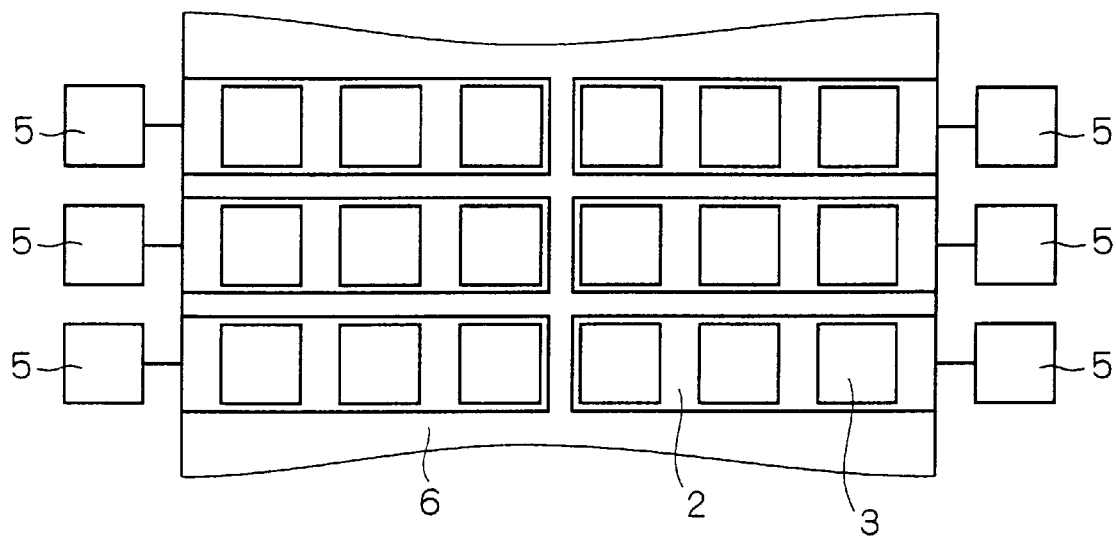
FIG. 20 is a top view of a test structure for insulation-film evaluation according to a sixth preferred embodiment of the present invention.

FIG. 20 is a top view of a test structure for insulation-film evaluation according to a sixth preferred embodiment of the present invention. As in the fifth preferred embodiment, a plurality of cells are arranged in the form of a matrix. For example, a matrix of cells with 3 rows and 6 columns is shown in FIG. 20. All the cells are divided into a plurality of groups each having one read circuit 5. In the case of FIG. 20, all the cells are divided by rows and the cells in each row are further divided into two, right and left. That is, all the cells are divided into six groups in total. Cells in the same group are connected in series by the active region, and cells in the different groups are electrically isolated from each other by the element isolation insulation film 6.

Figure 21:
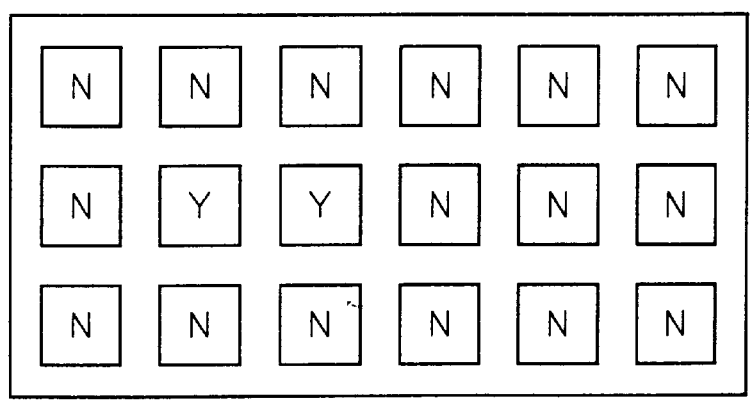
FIG. 21 shows a display matrix of the locations of failures.

The test structure of the sixth preferred embodiment is structurally more complicated than that of the fifth preferred embodiment since the number of read circuits 5 is increased by the number of groups to be divided. However, failure location is independently performed for each group as shown in FIG. 21, which increases accuracy in location.

Seventh Preferred Embodiment

Figure 22:
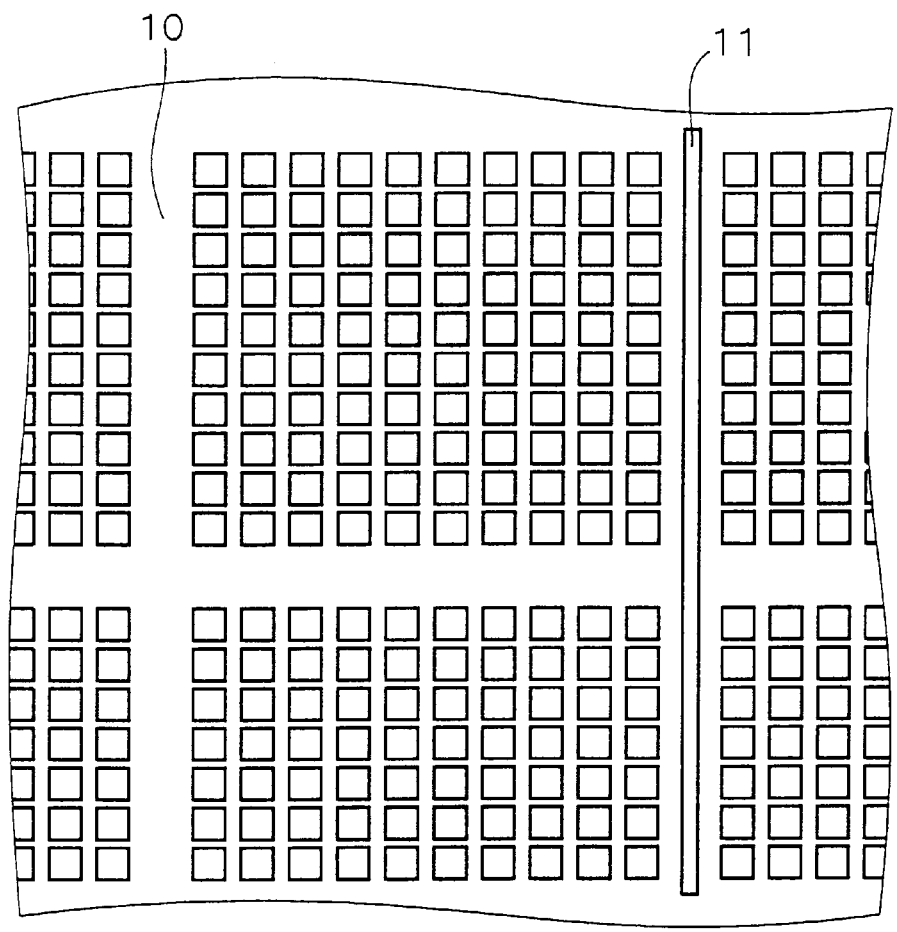
FIG. 22 is a top view of a test structure for insulation-film evaluation according to a seventh preferred embodiment of the present invention.

FIG. 22 is a top view of a test structure for insulation-film evaluation according to a seventh preferred embodiment of the present invention. In the aforementioned test structures of the first to sixth preferred embodiments, a failure in the gate insulating film 2 is located by electrical readout using the read circuit 5. The detected failure is then observed by a device such as an SEM for concrete failure analysis. It is, however, not always easy to bring the detected failure into a visual field of the SEM by manual operation, especially for devices with a number of cells arranged in the form of a matrix. For this reason, a mark is previously put at predetermined blocks as shown in FIG. 22 (e.g., gap 10 around an array with 10 rows and 10 columns or a dummy pattern 11 every 100 rows).

According to the test structure of the seventh preferred embodiment, for failure observations using an SEM after location of failures, an operator can look to a mark on the test structure to recognize the locations of failures in the gate insulating film 2. This simplifies the operation of entering the detected failures within the visual field of the SEM. The same applies to the following eighth to tenth preferred embodiments.

Figure 23:
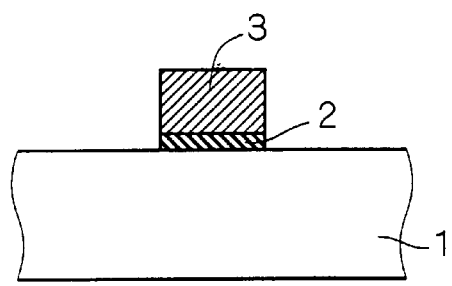
FIG. 23 is a cross-sectional view of another cell structure.

In the cell structure of the aforementioned first to seventh preferred embodiments, the gate insulating film 2 is formed across the surface of the semiconductor substrate 1 in the active region and the gate electrodes 3 are selectively formed on the gate insulating film 2 as shown in FIG. 3. It should be understood that the present invention is not limited to this structure, but also applicable to a cell structure wherein a multilayer structure with the gate insulating film 2 and the gate electrode 3 of the same sectional shape stacked in this order is selectively formed on the semiconductor substrate 1 as shown in FIG. 23. The same applies to the following eighth to tenth preferred embodiments.

Eighth Preferred Embodiment

An eighth preferred embodiment gives another example of a two-phase CCD structure adopted as the test structure for insulation-film evaluation as in the second preferred embodiment.

Figure 24:
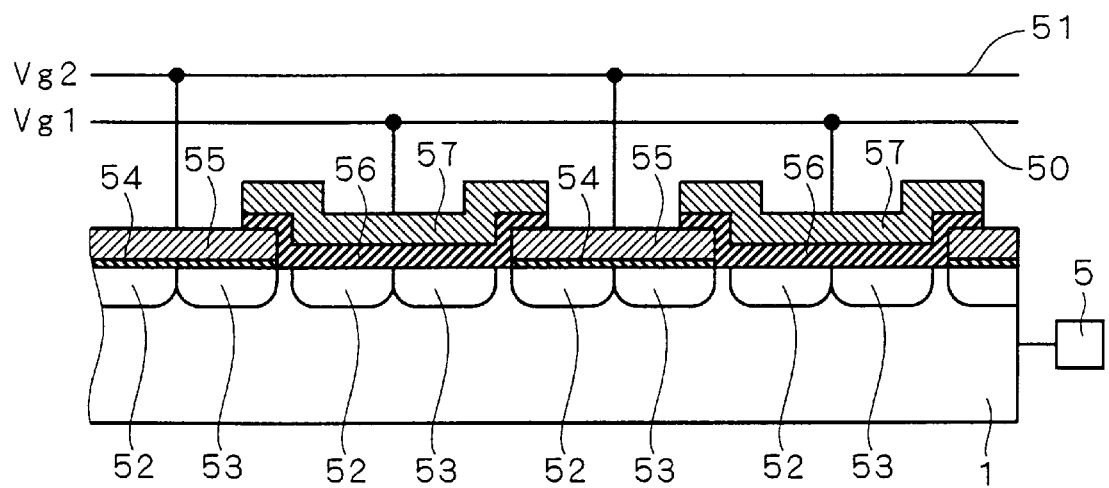
FIG. 24 is a cross-sectional view of a test structure for insulation-film evaluation according to an eighth preferred embodiment of the present invention.

FIG. 24 is a cross-sectional view of a test structure for insulation-film evaluation according to the eighth preferred embodiment of the present invention. Of a gate-electrode array consisting of a plurality of gate electrodes, four electrodes aligned in this order are shown in FIG. 24. On the main surface of the semiconductor substrate 1, a gate insulating film 54 is selectively formed, on which a gate electrode 55 is formed. The gate electrode 55 is connected to a wire 51. In the main surface of the semiconductor substrate 1 under the gate electrode 55, two ion-implanted regions 52, 53 with different impurity concentrations are aligned. This structurally provides the potential difference between the portion where the ion-implanted region 52 is formed and the portion where the ion-implanted region 53 is formed, under the gate electrode 55.

On the main surface of the semiconductor substrate 1 where the gate insulating film 54 is not formed, a gate insulating film 56 having a greater thickness than the gate insulating film 54 is formed. Further, a gate electrode 57 connected to a wire 50 is formed on the gate insulating film 56. In the main surface of the semiconductor substrate 1 under the gate electrode 57, two ion-implanted regions 52, 53 with different impurity concentrations are aligned as under the gate electrode 55. This structurally provides the potential difference between the portion where the ion-implanted region 52 is formed and the portion where the ion-implanted region 53 is formed, under the gate electrode 57.

Alternatively, the gate electrode 55 on the left and the gate electrode 55 on the right in FIG. 24 may be different in form. The same can be said of the gate electrodes 57.

In the test structure of the eighth preferred embodiment, there is the potential difference between the portion where the ion-implanted region 52 is formed and the portion where the ion-implanted region 53 is formed, under the gate electrodes 55, 57. Accordingly, the charge 9 supplied from the locations of failures in the gate insulating films 54, 56 into the semiconductor substrate 1 can sequentially be transferred by simple two-phase operations using the wires 50, 51 of a two-input system. This allows the read circuit 5 to find the locations of failure.

Also, the gate insulating films 55, 56 of different thicknesses can be evaluated independently using a single test structure.

Ninth Preferred Embodiment

We will now consider the case where the gate insulating film 2 suffers a severe dielectric breakdown by the application of stress and too much charge 9 is supplied from the gate electrode 3 into the semiconductor substrate 1 in finding the locations of failures in the structure of FIG. 2, for example. In this case, if the high amount of supplied charge 9 flows out of a potential well under the failed part of the gate insulating film 2, flowing into the adjacent potential well, it may become difficult to specify the locations of failures. A ninth preferred embodiment proposes a test structure capable of previously avoiding such a problem.

Figure 25:
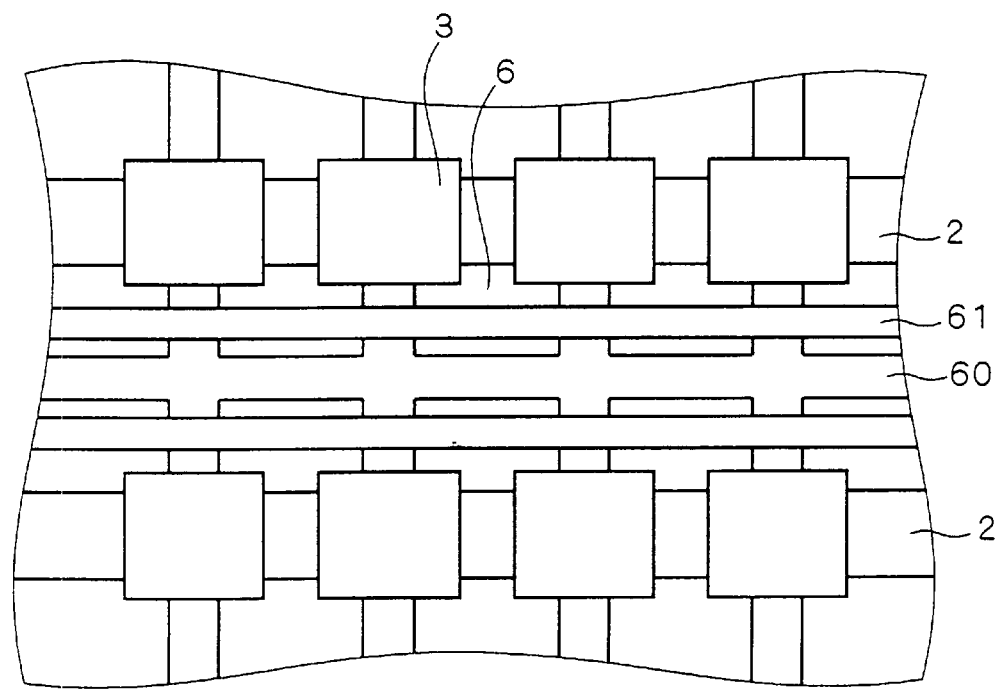
FIG. 25 is a top view of a test structure for insulation-film evaluation according to a ninth preferred embodiment of the present invention.

FIG. 25 is a top view of a test structure for insulation-film evaluation according to the ninth preferred embodiment of the present invention. In the main surface of the semiconductor substrate 1, an overflow drain region 60 is formed. The overflow drain region 60 includes a stem portion formed in parallel with a gate-electrode array, and branch portions branched from the stem portion and connected to the main surface of the semiconductor substrate 1 under the gate electrodes 3. On the main surface of the semiconductor substrate 1, an overflow gate electrode 61 is formed, extending in parallel with the gate-electrode array and crossing over the branch portions of the overflow drain region 60. For failure location, a predetermined voltage is applied to the overflow drain region 60 and the overflow gate electrode 61.

While the end portion of the gate electrode 3 in FIG. 25 extends over the end portion of the element isolation insulation film 6, it may be within the active region as shown in FIG. 2.

In the test structure of the ninth preferred embodiment, even if a high amount of charge 9 is supplied into the semiconductor substrate 1 for failure location and flows out of the potential well under the failed part of the gate insulating film 2, the overflowing charge 9 can be drawn to the overflow drain region 60 by the application of an appropriate voltage to the overflow drain region 60 and the overflow gate electrode 61. This previously prevents the aforementioned problem and improves accuracy in failure location in the gate insulating film 2.

Tenth Preferred Embodiment

Figure 26:
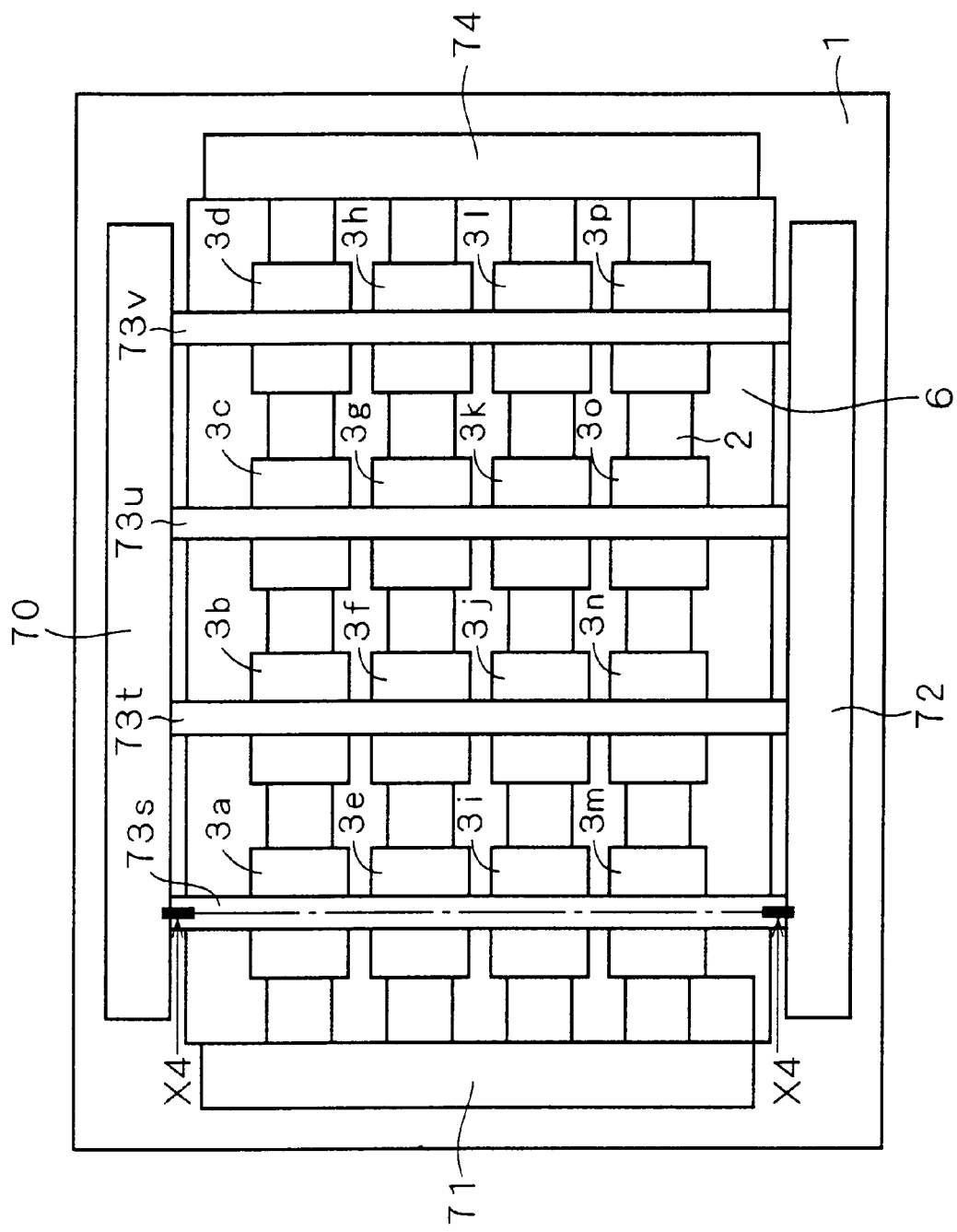
FIG. 26 is a top view of a test structure for insulation-film evaluation according to a tenth preferred embodiment of the present invention

FIG. 26 is a top view of a test structure for insulation-film evaluation according to a tenth preferred embodiment of the present invention. In FIG. 26, sixteen gate electrodes 3a to 3p are arranged in the form of a matrix with 4 rows and 4 columns. On the main surface of the semiconductor substrate 1 in the active region, the gate insulating film 2 is formed, on which gate electrodes 3a to 3p are formed. The element isolation insulation film 6 provides electrical isolation between each row in the gate-electrode matrix.

The semiconductor substrate 1 is provided with an X shift register 70, a Y stress applying circuit 71, an X stress applying circuit 72, and a Y shift register 74. The X shift register 70 and the X stress applying circuit 72 are connected to wires 73s to 73v each connected to the gate electrodes 3a to 3p in each column of the gate-electrode matrix by contact holes (not shown). The Y stress applying circuit 71 and the Y shift register 74 are electrically connected to the active region of the semiconductor substrate 1 for each row of the gate-electrode matrix.

Figure 27:
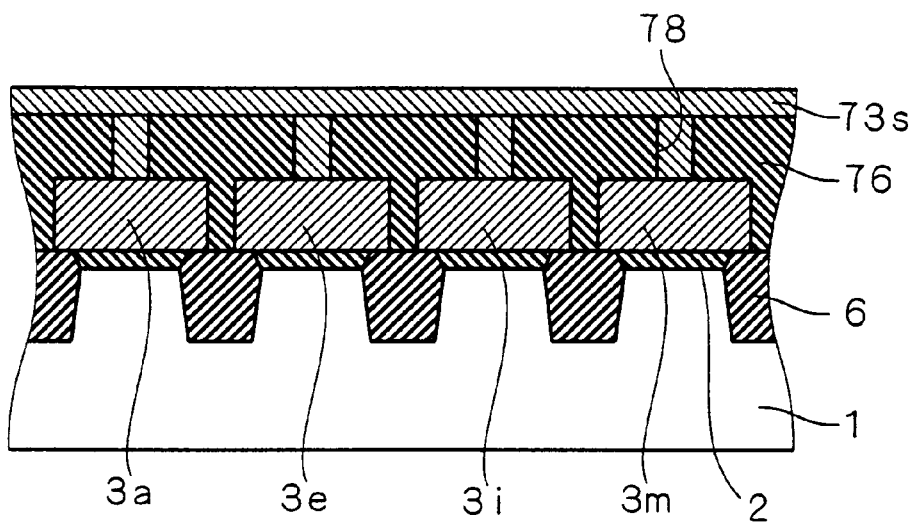
FIG. 27 is a cross-sectional view taken along the line X4 in FIG. 26.
Figure 28:
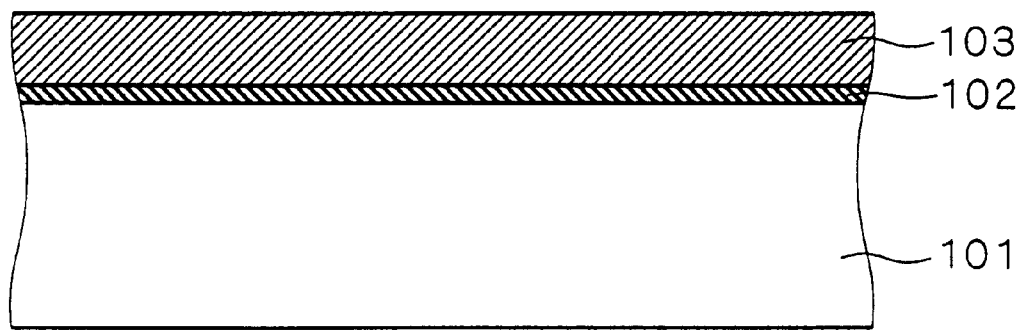
FIG. 28 is a cross-sectional view of a conventional test structure for insulation-film evaluation.

FIG. 27 is a cross-sectional view taken along the line X4 in FIG. 26. On the gate electrodes 3a, 3e, 3i, 3m, an interlayer insulation film 76 is formed, on which the wire 73s is formed. The wire 73s and the gate electrodes 3a, 3e, 3i, 3m are formed in the interlayer insulation film 76 and connected to each other by conductor-filled contact holes 78.

Referring now to FIG. 26, we will describe a technique of the TDDB test using the test structure of the tenth preferred embodiment. First, a voltage is applied from the X stress applying circuit 72 through the wires 73s to 73v to the gate electrodes 3a to 3p, or a predetermined voltage is applied from the Y stress applying circuit 71 to the active region of the semiconductor substrate 1. By so doing, predetermined evaluation stress is applied to the gate insulating film 2.

Next is to find the locations of failures. The Y shift register 74 selects, for example, the top row of the gate-electrode matrix, and the X shift register 70 applies a voltage to the gate electrode 3a through the wire 73s. When the gate insulating film 2 under the gate electrode 3a suffers a breakdown by the application of evaluation stress, current flows from the gate electrode 3a through the gate insulating film 2 to the active region of the semiconductor substrate 1. This flow of current is detected by the Y shift register 74. When no breakdown occurs in the gate insulating film 2 under the gate electrode 3a, on the other hand, no current flow occurs from the gate electrode 3a to the active region of the semiconductor substrate 1. In this fashion, whether the gate insulating film 2 suffers a breakdown or not can be evaluated from the presence or absence of current flow from the gate electrode 3a to the semiconductor substrate 1.

Under the same condition where the Y shift register 74 selects the top row of the gate-electrode matrix, the X shift register 70 applies a voltage to the gate electrode 3b through the wire 73t. In the same manner as described above, whether the gate insulating film 2 under the gate electrode 3b suffers a breakdown or not is evaluated. These operations are repeated until the evaluation of the gate insulating film 2 under the gate electrode 3d is completed.

After the evaluation of the top row of the gate-electrode matrix is completed, the Y shift register 74 selects the second top row in FIG. 26. Like the top row, the second row is evaluated from the gate electrode 3e in sequence. The operations are repeated until all the rows are evaluated.

In the test structure for a matrix of gate electrodes according to the tenth preferred embodiment, the row and column of the gate-electrode matrix in which the gate insulating film 2 suffers a breakdown can be detected by varying combinations of selections by the X shift register 70 and the Y shift register 74. In other words, the location of a failure in the gate insulating film 2 can be recognized as an address (X, Y). This simplifies the operation of failure location.

Alternatively, the thickness of the gate insulating film 2 and the form of the gate electrodes 3a to 3p may vary for each row, and the form of the element isolation insulation film 6 may vary for each row. This allows various types of gate insulating films 2 to be evaluated using a single test structure.

Further, instead of applying a common voltage to all the gate electrodes 3a to 3p, the X stress applying circuit 72 and the Y stress applying circuit 71 may be divided by columns and rows of the gate-electrode matrix, respectively, so that they can apply a voltage for each column/row or for a combination of several columns/rows. In this case, evaluation stress can be applied for each desired column/row or can be applied only on a desired gate electrode, which increases flexibility in evaluation.

While the invention has been shown and described in detail, the foregoing description is in all aspects illustrative and not restrictive. It is therefore understood that numerous modifications and variations can be devised without departing from the scope of the invention.

What is claimed is:

1. A test structure for insulation-film evaluation comprising:
   a substrate;
   an insulation film to be evaluated which is formed on a main surface of said substrate;
   an electrode array formed on said insulation film and consisting of a plurality of electrodes arranged in spaced manner,
   a plurality of wires for applying a voltage to said plurality of electrodes, said voltage including a voltage for applying evaluation stress to said insulation film and a voltage for sequentially transferring charge generated in breakdown part of said insulation film along said electrode array to detect the presence or absence of breakdown in said insulation film due to the application of said evaluation stress; and
   a read circuit for sequentially reading the presence or absence of the transfer of said charge.

2. The test structure according to claim 1, wherein adjacent three of said electrodes in said electrode array are connected to different ones of said wires.

3. The test structure according to claim 1, wherein said electrode array consists of said electrodes under which an impurity region is formed in said main surface of said substrate and said electrodes under which said impurity region is not formed in said main surface of said substrate, which are aligned alternately.

4. The test structure according to claim 1, wherein said electrode array consists of said electrodes doped with impurities and said electrodes not doped with said impurities, which are aligned alternately.

5. The test structure according to claim 1, wherein adjacent four of said electrodes in the electrode array are connected to different ones of said wires.

6. The test structure according to claim 1, wherein said electrode array consists of first electrodes and second electrodes which are aligned alternately, said first electrodes formed on a thin-film portion of said insulation film having a first thickness, said second electrodes formed on a thick-film portion of said insulation film having a second thickness larger than said first thickness; and
   adjacent four of said electrodes in said electrode array are connected to different ones of said wires.

7. The test structure according to claim 6, wherein said second electrodes extend over the end portions of said first electrodes.

8. The test structure according to claim 1, wherein a plurality of impurity regions with different impurity concentrations are adjacently formed in said main surface of said substrate under each of said electrodes.

9. The test structure according to claim 1, further comprising:
   a drawn region formed along said electrode array in said main surface of said substrate, for drawing charge flowing out of a potential well under breakdown part of said insulation film caused by the application of said evaluation stress.

10. The test structure according to claim 1, wherein said substrate includes an element isolation region where an element isolation insulation film is formed, and an active region defined by said element isolation insulation film; and
    the end portions of said electrodes are within said active region.

11. The test structure according to claim 1, wherein said substrate includes an element isolation region where an element isolation insulation film is formed, and an active region defined by said element isolation insulation film; and
    said electrodes extend over a boundary between said element isolation region and said active region.

12. The test structure according to claim 1, wherein cells including said electrodes are arranged in the form of a matrix, all of said cells being electrically connected to each other by an active region of said substrate.

13. The test structure according to claim 1, wherein cells including said electrodes are arranged in the form of a matrix, a plurality of said cells being divided into a plurality of groups by an element isolation region of said substrate; and
    said read circuit is provided for each of said groups.

14. The test structure according to claim 1, wherein cells including said electrodes are arranged in the form of a matrix; and
    a mark is provided at predetermined blocks on said substrate.

15. A test structure for insulation-film evaluation, comprising:
    a substrate;
    an insulation film to be evaluated which is formed on a main surface of said substrate;
    an electrode matrix consisting of a plurality of electrodes formed in the form of a matrix on said insulation film;
    a stress applying circuit for applying evaluation stress to said insulation film;

a first shift register capable of applying a voltage to said plurality of electrodes for each column of said electrode matrix; and a second shift register which is electrically connected to said substrate for each row of said electrode matrix and capable of detecting whether or not the application of said voltage by said first register causes current flow to said substrate through said insulation film.

16. The test structure according to claim 15, wherein said electrode matrix includes at least two rows having said insulation film of different thicknesses.

17. The test structure according to claim 15, wherein cells including said electrodes are arranged in the form of a matrix; and a mark is provided at predetermined blocks on said substrate.

* * * * *